United States Patent [19]

Brana et al.

[11] Patent Number: 5,420,137
[45] Date of Patent: May 30, 1995

[54] AMONAFIDE SALTS

[75] Inventors: Miguel F. Brana; Jose M. C. Berlanga, both of Madrid, Spain; Reinhard Spengler; Christine Tetzner, both of Ludwigshafen, Germany

[73] Assignee: Knoll AG, Ludwigshafen, Germany

[21] Appl. No.: 262,387

[22] Filed: Jun. 20, 1994

Related U.S. Application Data

[63] Continuation of Ser. No. 118,776, Sep. 10, 1993, abandoned, which is a continuation of Ser. No. 781,129, filed as PCT/EP90/01088, Jul. 6, 1990, published as WO 91/00857, Jan. 24, 1991, abandoned.

[30] Foreign Application Priority Data

Jul. 11, 1989 [DE] Germany .................. 39 22 771.5

[51] Int. Cl.$^6$ .................. C07D 221/14; A61K 31/47
[52] U.S. Cl. .................. 514/296; 546/100
[58] Field of Search .................. 546/100; 514/296

[56] References Cited

U.S. PATENT DOCUMENTS 5,086,059  2/1992  Ardecky .................. 546/99

FOREIGN PATENT DOCUMENTS 125439    11/1984  European Pat. Off.
2423547   5/1974   Germany.
1602683   11/1981  United Kingdom.
90-02163  7/1991   WIPO.

OTHER PUBLICATIONS

Sheithauer, Breast Cancer Research and Treatment 20, 63–67 (1991).
Kornek, Europ. J. Cancer 30A (3) 398–400 (1994).
Brana European Journal of Medicinal Chemistry, Chim. Ther. 16, 207 (1981).

*Primary Examiner*—Mark L. Berch
*Attorney, Agent, or Firm*—Keil & Weinkauf

[57] ABSTRACT

The monohydrochloride and the monomethanesulfonate of amonafide are described. The salts have good pharmaceutical properties besides their antitumor action.

4 Claims, No Drawings

AMONAFIDE SALTS

This application is a continuation of application Ser. No. 08/118,776, filed on Sep. 10, 1993, abandoned, which is a continuation of application Ser. No. 07/781,129, filed as PCT/EP90/01088, Jul. 6, 1990, published as WO 91/00857, Jan. 24, 1991, abandoned.

DESCRIPTION

The present invention relates to novel salts of amonafide.

Amonafide (Eur. J. Med. Chem. Chim. Ther. 16, 209 (1981)) is a substance which has antitumor action. It exists in the form of very fine needle-like yellow crystals which are reminiscent of asbestos and are very difficult to process to oral forms or injection solutions.

Attempts to react amonafide with acids such as hydrochloric acid or methanesulfonic acid result in salts which, because of their strongly acidic properties, are unsuitable for the preparation of pharmaceutical forms. The reason for this is that the salts elicit irritant effects because of their strongly acidic nature. An additional factor is that they are incompatible with many pharmaceutical auxiliaries required for preparing capsules.

It has now been found that although certain salts of amonafide do not have the abovementioned adverse properties, they do not differ from amonafide in terms of the antitumor action.

The invention relates to salts of amonafide of the formula

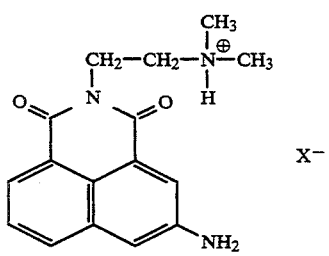

in which $X^-$ is a $Cl^-$ or $CH_3-SO_3^-$ ion. stable in the dark, and in solid form they can easily be metered, are free-flowing, readily compressible and only moderately hygroscopic and easy to dry. They have the further advantage that they are compatible with gelatin so that they can easily be processed to soft and hard gelatin capsules. The latter particularly applies to the monohydrochloride.

The salts are prepared by reacting amonafide with the calculated amount of acid. The salt formation preferably takes place in alcoholic solution.

Examples 1 and 2 show the preparation of the novel salts:

3 g of amonafide were dissolved under reflux in 60 ml of virtually anhydrous ethanol. Subsequently 1 ml of 35% strength hydrochloric acid was added dropwise while shaking vigorously. After cooling, the resulting crystals were filtered off and washed with 10 ml of anhydrous ethanol. 3.1 g (93%) of amonafide monohydrochloride were obtained ($C_{16}H_{18}ClN_3O_2$), melting point=290° C.

Example 2

3.4 g (85%) of amonafide monomethanesulfonate, melting point=255° C., are obtained in analogy to Example 1 by reaction with 0.8 ml of methanesulfonic acid.

The following examples show the good pharmaceutical processability of the novel salts:

Example A

Preparation of amonafide tablets

| | |
|---|---|
| Amonafide.HCl | 288.4 mg |
| D-mannitol | 40.6 mg |
| Polyvinylpyrroldone [sic] | 13.0 mg |
| Microcrystalline cellulose | 20.0 mg |
| Sodium carboxymethylstarch | 10.0 mg |
| Highly disperse silica | 2.0 mg |
| Talc | 4.0 mg |
| Magnesium stearate | 2.0 mg |
| | 380.0 mg |

Granules were obtained by granulation of active substance and mannitol with the aid of polyvinylpyrrolidone and, after mixing with the other substances mentioned, were readily converted into tablets in conventional tablet presses. Used as tableting tool were 11 mm round punches. The tablet disintegration time was 9 min.

The polyvinylpyrrolidone used had the viscosity of 20 mPa.sec in a 20% strength aqueous solution at 25° C.

Example B

Preparation of film-coated tablets

Tablets from Example A were coated with a coating of the following composition until the weight gain per tablet core was found to be about 20–30 mg:

| | |
|---|---|
| Hydroxypropylmethylcellulose | 0.064 kg |
| Polyethylene glycol with the average molecular weight 8000 | 0.040 kg |
| Talc | 0.080 kg |
| Titanium dioxide | 0.020 kg |
| Sodium lauryl sulfate | 0.002 kg |
| Ethanol | 0.794 kg |

Example C

Preparation of enteric tablets

Tablets from Example A were coated with a coating of the following composition until the weight gain per tablet core was found to be about 40–50 mg.

| | |
|---|---|
| Hydroxypropylmethylcellulose phthalate | 0.1620 kg |
| Dibutyl phthalate | 0.0324 kg |
| Acetone | 0.8826 kg |
| Isopropanol | 0.8826 kg |
| Coloring pigment | 0.0404 kg |

Example D

Preparation of an injection solution as concentrate

| | |
|---|---|
| Amonafide.HCl | 564.3 mg |
| Water for injection ad 10 ml | |

The solution was sterilized by filtration, dispensed into 10 ml brown glass ampoules and autoclaved.

Example E

Preparation of amonafide injection concentrate as lyophilisate

| Amonafide.2HCl | 2.992 kg |
| NaOH, 5 m | 1.998 kg |
| Water for injection ad | 20.000 kg |

The solution was sterilized by filtration and subsequently dispensed in 2 ml portions into vials of glass type I (brown glass) and freeze-dried. The pH of the reconstituted solution was 5.5±0.5, the osmolarity was about 1,000 mosmol/kg and the residual moisture was about 1%.

The amonafide was in the form of the monohydrochloride in the concentrate.

Example F

Preparation of soft gelatin capsules

| Amonafide.HCl | 28.2 g |
| Silicone oil ad | 100.0 g |

The homogeneous suspended composition was dispensed into soft gelatin capsules of size 16 minims.

We claim:

1. A salt of amonafide of the formula

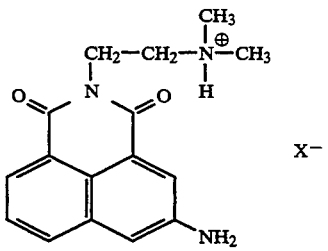

in which X⁻ is a Cl⁻ or CH₃—SO₃⁻ ion.

2. Amonafide monohydrochloride.

3. An antitumor composition which comprises an antitumor effective amount of the monohydrochloride salt of amonafide and a pharmaceutical auxiliary and/or carrier.

4. An antitumor composition which comprises an antitumor effective amount of the monomethanesulfonate salt of amonafide and a pharmaceutical auxiliary and/or carrier.

* * * * *